US005984926A

United States Patent [19]
Jones

[11] Patent Number: 5,984,926
[45] Date of Patent: Nov. 16, 1999

[54] BONE SCREW SHIMMING AND BONE GRAFT CONTAINMENT SYSTEM AND METHOD

[76] Inventor: A. Alexander M. Jones, P/SL Professional Plaza W., 1601 E. 19th Ave. Suite 5000, Denver, Colo. 80218

[21] Appl. No.: 09/028,968

[22] Filed: Feb. 24, 1998

[51] Int. Cl.⁶ .................................................. A61B 17/56
[52] U.S. Cl. ............................................. 606/72; 606/76
[58] Field of Search ............................... 606/72, 76, 77, 606/154, 229, 230, 231

[56] References Cited

U.S. PATENT DOCUMENTS

| | | | |
|---|---|---|---|
| 4,182,339 | 1/1980 | Hardy, Jr. .................................. | 128/334 |
| 4,205,399 | 6/1980 | Shalaby et al. .......................... | 128/335 |
| 4,394,370 | 7/1983 | Jefferies .................................... | 414/15 |
| 4,520,821 | 6/1985 | Schmidt et al. .......................... | 128/334 |
| 4,563,489 | 1/1986 | Urist ........................................... | 524/21 |
| 5,059,211 | 10/1991 | Stack et al. ............................... | 606/198 |
| 5,628,788 | 5/1997 | Pinchuk ..................................... | 606/194 |
| 5,756,457 | 5/1998 | Wang et al. ............................... | 606/152 |
| 5,876,432 | 3/1999 | Lau et al. .................................. | 606/191 |

Primary Examiner—Michael Buiz
Assistant Examiner—Jonathan D. Goldberg
Attorney, Agent, or Firm—Ramon L. Pizarro; Edwin H. Crabtree

[57] ABSTRACT

A system and method for shimming a hole drilled in a bone for the insertion of an orthopedic screw. The system includes a sleeve with an elongated sleeve shaped body having an external surface and an internal surface, a first end, a mid portion, and a second end. The mid portion of the body is made from woven fibers that are free to move relative to one another and being woven in a crisscrossing spiral arrangement along the sleeve shaped body. The first end of the body includes an opening that can accept a rod. The second end of the body is smaller than the first end of the body, so that the first end of the sleeve shaped body may be inserted into the hole with the aid of the rod, and so that when the orthopedic screw is inserted into the elongated sleeve the woven fibers of the body will move relative to one other to accommodate the orthopedic screw and take up any space between the screw and the hole.

16 Claims, 4 Drawing Sheets

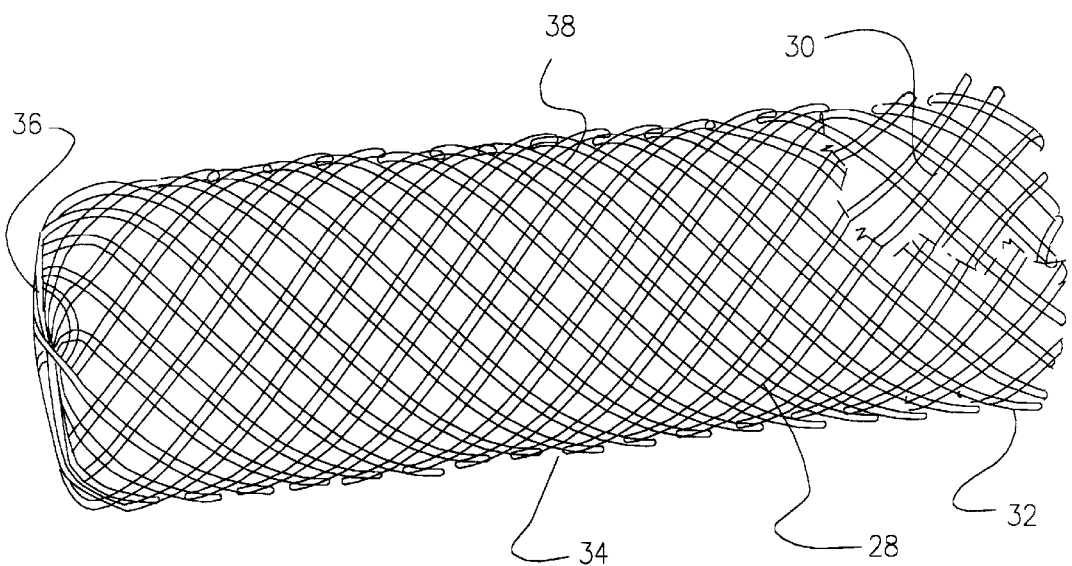
Fig. 2
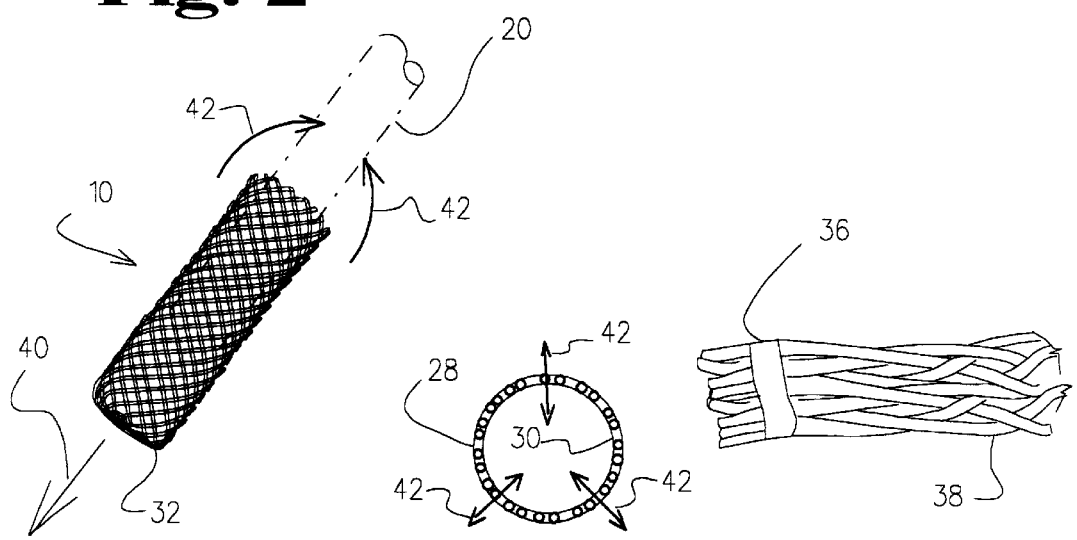
Fig. 3  Fig. 3A  Fig. 3B

BONE SCREW SHIMMING AND BONE GRAFT CONTAINMENT SYSTEM AND METHOD

BACKGROUND OF THE INVENTION (a) Field of the Invention

This invention generally relates to a device and a method which allows the accommodation of an orthopedic screw into a bone hole. More particularly, but not by way of limitation, the instant invention relates to a self adjusting system and method that includes a woven sleeve for shimming and salvaging holes for orthopedic fasteners, and for accepting and strengthening the grip of orthopedic fasteners. Additionally, the invention includes a system for delivering bone strengthening material, such as morselized bone graft material, to a location in a patient.

(b) Discussion of Known Art

The treatment of fractures frequently requires the attachment of a plate to the bone in order to ensure the correct positioning of the sections of bone that are to be fused together. To attach the plate to the bone one typically selects a plate which has pre-drilled screw hole locations. These pre-drilled screw holes are of a size that accepts a specific size of screw. Additionally, the plate also matches the size and type of bone being worked on. In order to produce the most secure attachment of the plate to the bone one should use screws which produce a close fit between the screw and the plate. The close fit between the screws and the plate results in a highly stable assembly. Unfortunately, however, the close fit that provides a stable connection provides little room for correction of imperfections in the holes drilled into the bone which should match the holes in the plate being attached to the bone. For example, slightly misplaced holes, holes which must be re-drilled, or screw holes which are stripped by over-zealous tightening of the screw, will effectively end up as being too large for ensuring the full engagement of the screw and the subsequent development of the full strength or stability which may be provided by the plate. Furthermore, depending on the brittleness of the patient's bone, the location on the bone, and the type of screw being used, or because of over-zealous tightening of the screw one may accidentally strip or damage the hole such that the full development of the strength and stability of the plate attachment is impossible to develop. Still further, bone is a non homogeneous, anisotropic material, exhibiting different strength properties depending on the direction of the stress imposed on the bone. These properties lead to bone fractures, or damaged screw holes, with seemingly random features.

To repair holes which have been damage if due to drilling, fracture, or stripping during the installation of orthopedic screws one may reposition the plate, or provide a plate with redundant holes which may be used for drilling additional screw holes in the bone for the attachment of screws to compensate for the improperly attached screws. Unfortunately, anatomic constraints and fracture configuration may limit possible screw placement sites. The original screw hole position may be the only feasible location for appropriate placement of the plate, making repair of the damaged hole the only desirable solution.

An approach at salvaging the damaged hole is the attempt to use a larger screw. However, the use of a larger screw is typically not possible due to the fact that the size of the screw, and hence the screw hole, are pre-determined by the plate being used. Of course, one may change the plate to the larger plate, for example, but this option is usually not available due to the size and location of the bone being repaired. Moreover, a larger screw may cause even greater damage to the bone being repaired. Finally, the anatomy of the location of being repaired may allow the use of a single diameter of screw. For example, the use of a large screw into the pedicle of a vertebra could break or split the pedicle.

There are several known devices designed for providing or enhancing the attachment orthopedic screws to bone. One example of these devices is shown in U.S. Pat. No. 5,084,050 to Draenert, which teaches the use of an implant that includes a sheath that holds a material that swells out once inserted in into the bone in order to provide a means for developing a firm support against the bone. This system is disadvantaged, however, due to the fact that it requires the drilling of a hole that is larger than the screw being used, and in that it does not provide an immediate secure hold against the bone. Furthermore, the Draenert device is limited in its applicability in that is primarily useful in situations where a new portion of bone is to be grown in order to support the screw. Still further, the principle operation of the Draenert device, which provides for a dowel shaped, hollow cylinder which expands to engage the surrounding bone, does not lend itself for a variety of situations, whether the situation requires the use of bone grafts or simply the accommodation of a screw where the screw hole is only slightly larger than the diameter of the screw threads.

It will become apparent that the Draenert device is almost of no use as a repair or salvaging device for situations where the hole for the screw has become damaged due to brittleness or excessive torque imposed on the screw. This is due to the fact that the damaged hole will have been originally made to correspond to the holes in the plate being attached to the bone. In other words, the damaged hole in the bone is likely to be larger than the hole through the plate; meaning that an insert such as the Draenert device would not fit through the hole in the plate. Therefore, in order to salvage the hole using the Draenert device the surgeon would have to remove the plate, adapt the hole so that it can receive the Draenert device, and then re-fasten the plate over the screw holes.

Another insert for use with bone screws in the repair of fractured bones is taught in U.S. Pat. No. 4,760,843 to Fischer et al. The Fischer patent teaches a connector with an aperture therethrough. The aperture is of a large diameter at one end and of a smaller diameter at the other end. This arrangement causes the end with the smaller diameter to expand once the bone screw is inserted into the device, gripping the inside of the hole in the bone. As can be understood from the above discussion, the use of an expanding device, such as the Fischer device, in situations where the patient's bone has already fragmented is likely to invoke even more than damage to the bone due to the fact that the hole is likely to be in brittle or soft bone. Thus, an attempt to repair a screw hole with the Fischer device is likely to result in even more damage to the hole. Still further, the Fischer device is nearly useless for the purpose of salvaging an existing hole during surgery. This is due to the fact that the stripped or damaged hole would be of a diameter that is approximately equal to the diameter of the hole through the plate; meaning that to salvage the hole, the surgeon would have to select the appropriate size Fischer connector and select a new screw that would cooperate with the Fischer connector. This is likely to produce a loose connection since the largest diameter of the plug sleeve portion of the device will necessarily be approximately the same size as the hole in the plate, preventing proper gripping of the bone immediately below the plate. Finally, an expanding device may fracture or "blow out" bone in certain anatomical area, such as the tube-like confines of the vertebral pedicles, and may increase the risk of injury to surrounding anatomical structures.

The devices for use in osteosynthesis include U.S. Pat. No. 5,275,601 to Gogolewski et al. The Gogolewski patent teaches the use of a self locking resorbable screw which is made of the material with a modulus that is similar to the modulus of bone. The Gogolewski patent, however, does not teach or suggest how to solve problems associated with salvaging a hole that has been damaged while attempting to fasten the screw within the hole.

Other approaches at ensuring that a bone screw is properly fastened or seated in the bone include the approach as taught in U.S. Pat. No. 5,607,304 to Bailey et al. where a threaded connector is used in combination with an implant to support a screw. Another example is found in U.S. Pat. No. 5,425,7762 to Cohen. The Cohen patent teaches the use of a pair of sections for surgical correction of damage to the bones of the digits of the foot. These patents, however, do not teach or suggest how to salvage a screw hole once it has become damaged due to a fracture of the sides of the hole.

Also of importance is the need for a device that can accommodate a wide variety of screws, and thus can be used with a variety of screws in a variety of applications. The ability of the device to accommodate a wide variety of screws allows the device to produce consistent, reliable results. Known devices, such as the Fischer device or the Draenert device, can complicate procedures and introduce the possibility of error due to the fact that they must be matched to a particular diameter of screw. Therefore, it is possible that the surgeon may find it necessary to remove one of the Fischer devices or the Draenert device after having inserted a device which is slightly smaller than the needed device.

Thus a review of known orthopedic devices reveals a need for a device and method for salvaging damaged holes that have been drilled into a patient's bone in order to attach a screw to the bone.

Still further, a review of known devices reveals a needed for a method and a system that allows the surgeon to salvage or correct a hole that has become enlarged by erosion of the sides of the hole.

Still further, there remains a need for a system for salvaging a hole by providing self adjusting shims that accommodate to the hole in a radial manner in order to prevent bunching or folding and accumulation of the shimming material.

There remains a need for a system and method for salvaging a damaged hole for an orthopedic fastener, the system and method allowing modification of the thickness and materials used in salvaging the hole.

There remains a need for a system and method for salvaging a damaged hole for an orthopedic fastener, without having to remove plates or other devices that have been successfully attached in order to access the damaged hole.

There remains a need for a system and method that cooperates with a screw being driven into a bone and allows a surgeon to tailor the amount and kind of agents used in attachment of the screw, and thus allowing the surgeon to create an asymmetrical insert, if necessary, to accommodate the needs of the patient.

SUMMARY

It has been discovered that the problems left unanswered by the known art can be solved with a device which includes an elongated sleeve shaped body, or "sock" shaped body, constructed from woven fibers, the fibers being free to move relative to one another and being woven in a crisscrossing spiral arrangement along the sleeve shaped body. In a highly preferred embodiment of the invention the sleeve shaped body is used in conjunction with a smooth rod that is used to insert the sleeve body into a damaged hole.

It is contemplated that the "screw sock" of the instant invention could be used in the following fashion. The surgeon, after realizing that the screw had inadequate grip of the bone, could remove the screw. The surgeon would then push the woven "screw sock" as taught herein down into the hole with the aid of the smooth rod. Thus, it should be understood that the flexibility and adjustability of the instant invention allows the insertion of the "screw sock" of the invention through a hole in the metal plate without the need for removing the plate in order to place and seat the insert or "screw sock" in the damaged hole.

The ability to repair or salvage a single hole without needing to remove other screws which have been successfully driven through the plate or other orthopedic device and into the bone is an important new and useful result that is achieved with the disclosed structure. Thus the disclosed structure produces important advantages and is an important advancement in the art, as the removal of other screws, which have been successfully attached, to obtain access to the damaged hole will result in damage by stripping or loss of purchase in the holes of successfully attached screws. Thus it will be understood that the instant invention allows the surgeon to place a desired number of sleeves or "screw socks" into the damaged hole and then reintroduce the original screw into the hole to realize enhanced screw purchase.

It should be noted that while it is contemplated that the fibers used to form the sleeve of the instant invention may be of a flexible, non-resilient material, important new and useful results can be achieved by using materials which exhibit some degree of resiliency or stiffness. An important new and useful result is that by binding fibers at one end of the sleeve, and arranging the angle of the fibers relative to one another, one may produce a sleeve that tends to remain in an open arrangement or in a closed arrangement. The open arrangement being particularly useful for situations where it is desired that the sleeve expand and grip the sides of the hole as it is inserted into the hole. The closed arrangement being particularly useful in situations where it is desired to have the sleeve grip a fastener as the fastener and the sleeve are inserted into a hole or a hole which already holds a sleeve in its expanded, open arrangement.

Additionally, it is contemplated that the fibers used in forming the body of the "screw sock" of the instant invention may be of a bioabsorbable or non-bioabsorbable material. Thus, the surgeon may keep a variety of the "screw socks" available in order to mix and stack a series of the sleeves to accommodate a screw and achieve the needed purchase.

Thus, it will be appreciated that the disclosed invention is particularly useful situations where it is necessary to salvage a screw fastener hole in a bone. The need to use the instant invention arising from damage to the hole caused by over tightening of a screw being driven into the hole, or due to fraying of the hole due to osteoporosis of the bone material. Moreover, the instant invention will allow the user to adapt an existing hole so that the hole can accept a fastener which would otherwise be too small for adequately gripping the sides of the hole.

It will be appreciated that an important aspect of the invention includes the use of woven fibers which can move relative to one another in order to adjust the diameter or size of the sleeve to accommodate for differences in the size of hole and fastener being used.

It is also important to note that the fact that a series of the sleeves or "screw socks" of the instant invention may be stacked within one another allows the surgeon to adjust the thickness and buildup of material to enhance the purchase of the screw. This stackability allows the achievement of important new and useful results in that a surgeon may place a collapsed sleeve within another sleeve, an external sleeve, and between the screw and the external sleeve in an asymmetrical fashion. This arrangement would allow the surgeon to repair an off centered or out of round screw hole. Clearly, the same principle could be used to place bone graft material, or other desired material, symmetrically or asymmetrically between the screw and the external sleeve.

Also of importance is that the instant invention satisfies the need for a system that includes a single sleeve made in accordance with the principles taught herein can accommodate a wide variety of screws, and thus can be used with a variety of screws in a variety of applications. Thus, the instant invention exhibits the ability to accommodate a wide variety of screws allows the device to produce consistent, reliable results.

Thus, the disclosed invention includes a device and method for salvaging damaged holes that have been drilled into a patient's bone in order to attach a plate to the bone. Particularly, the instant invention allows a surgeon to salvage or correct a hole that has become enlarged by erosion of the sides of the hole.

Still further, the instant invention satisfies the need for a system for salvaging a hole by providing system including self adjusting shims that accommodate to the hole in a radial manner in order to prevent bunching, or folded and uneven accumulation of the shimming material.

Furthermore, it will be appreciated that the disclosed system and method for salvaging a damaged hole for an orthopedic fastener allows stacking of the sleeves, which in turn allows modification of the thickness and materials used in salvaging the hole.

In light of the above and accompanying description, it will be appreciated that the disclosed invention may be used in tendon or ligament reattachment procedures. These procedures typically involve the forming of a bore or tunnel that accepts means for anchoring and reattaching the ligaments to the bone. The anchoring means used in these ligament reattachment procedures may also work come loose due to over-tightening of threaded anchors, for example. Thus it can be appreciated that the instant invention can be used to salvage or bolster the attachment of these means used to anchor or reattach the ligaments to the bone. It is contemplated that the reattachment or enhancement of the grip of the anchor used in the ligament reattachment procedure would be carried out in a manner similar to the manner in which screw holes are salvaged as taught herein.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it is understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which:

FIG. 2 is a perspective view of a preferred embodiment of a sleeve made in accordance with the principles disclosed herein.

FIG. 3 illustrates the adjustment or expandability of the sleeve in an axial direction.

FIG. 3A illustrates the adjustment or expandability of the sleeve in a radial direction.

FIG. 3B illustrates the attachment of the fibers to achieve a body which tends to remain closed.

DETAILED DESCRIPTION OF PREFERRED EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
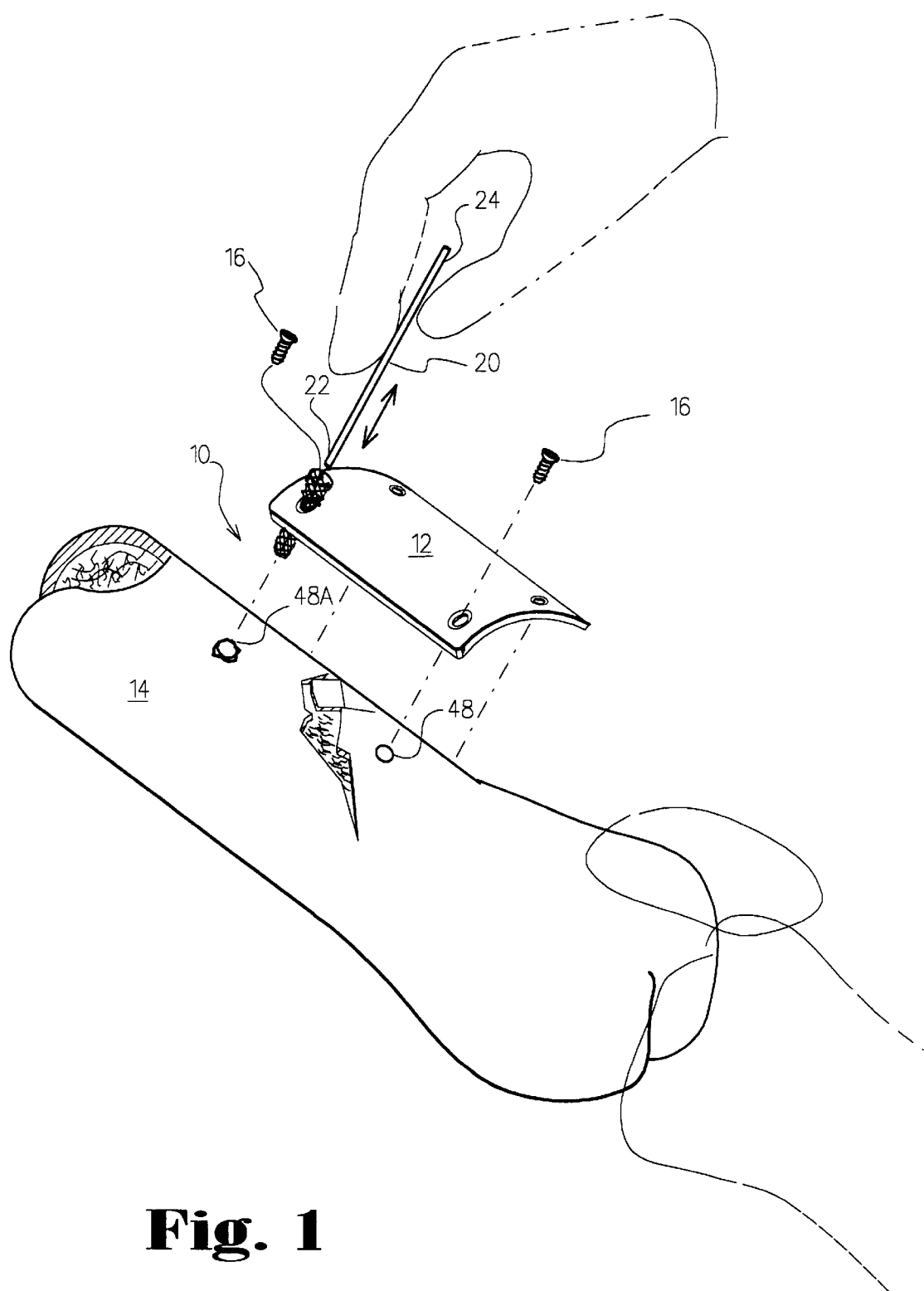
FIG. 1 is a perspective view showing the arrangement and use of the instant invention together with a plate.

Turning now to FIG. 1 where a preferred embodiment of the sleeve 10 of the instant invention has been shown in relation to a plate 12 which is to be mounted on to a bone 14 by means of fasteners 16. As can be observed from FIG. 1, the plate 12 includes a curvature that has been adapted for the bone to which is to be mounted. Is to be understood that the use of plates, such as the plate 12 shown on FIG. 1, is common practice in situations where a severe fracture is to be stabilized by the plate, or situations where several sections of bone or several different bones are to be stabilized in order to allow the healing between the sections of bone. Thus it will be appreciated that for a particular bone there is likely to be a single plate that will fit properly over the bone, and a specific plate may only have faster holes at locations which may not necessarily avoid the fractured or injured areas of the bone.

To fasten the plate to the bone, the surgeon must drill holes, such as hole 48 into the bone 14 to at locations that match the hole locations on the plate. The plate is then placed over the desired area and fastened in place with orthopedic or bone screws. As discussed earlier, the situation arises where while driving the screws 16 into the bone the hole 48 becomes stripped or enlarged. In the following discussion a damaged hole, or any hole which may benefit from the use of the instant invention, such as the hole used for anchoring a ligament or tendon, will be referred to as a damaged hole 48A. It is important to emphasize that it is contemplated that the instant invention may be used in any situation where it is desired to enhance the grip of the fastening means, and that it has been discovered that the instant invention is particularly useful in situations where the hole has been damaged, but it is contemplated that the instant invention may also be used with unstripped or undamaged holes. Accordingly, to salvage the damaged hole 48A, the sleeve 10 is driven into the hole 48A by means of a rod 20. The rod 20 will preferably include a first end 22 and a second end 24. The first end 22 will preferably include a smooth, rounded surface. The second end 24 may include the handle or other means for gripping the rod 20.

Turning now to FIG. 2 it will be understood that the sleeve 10 includes a sleeve shaped body 26. The sleeve shaped body 26 includes an external surface 28, as well as an internal surface 30, a first end 32, a mid portion 34, and a second end 36. The second end 36 will preferably include means for engaging the first end 22 of the rod 20. In a highly preferred embodiment of the invention these means include sleeve shaped body 26 with a second end 36 that is at least partially closed. Thus it is contemplated that the sleeve 10 will include a second end 36 that is smaller than the first end 32, or with the second end 36 being completely closed off as shown in the highly preferred embodiment of the appended drawings. Additionally, it is contemplated that the first end 32 of the sleeve 10 may be of a generally flared configuration to facilitate acceptance of the rod 20.

In a highly preferred embodiment of the invention the sleeve shaped body 26 will be made of woven fibers 38 which are free to move or slide relative to one another. As shown in the accompanying drawings, the woven fibers 38 form the sleeve shaped body 26 through a crisscrossing spiral arrangement in which the fibers are arranged in a helical spiral along the body 26. This general helical arrangement, coupled with the fact that the fibers will preferably be free to move relative to another, will allow the sleeve shaped body 26 to adjust and accommodate the fastener to be inserted therein, the rod, as well as the hole in which it is being inserted. It is also important to note that the woven structure will allow vascular and bony ingrowth, providing highly advantageous conditions for the integral re-generation of tissue and bone about the device. In a highly preferred embodiment of the invention the fibers of the sleeve 10 comprise suture material. However, it is contemplated that the sleeve 10 may be made from other medical fiber materials.

Figure 3C:
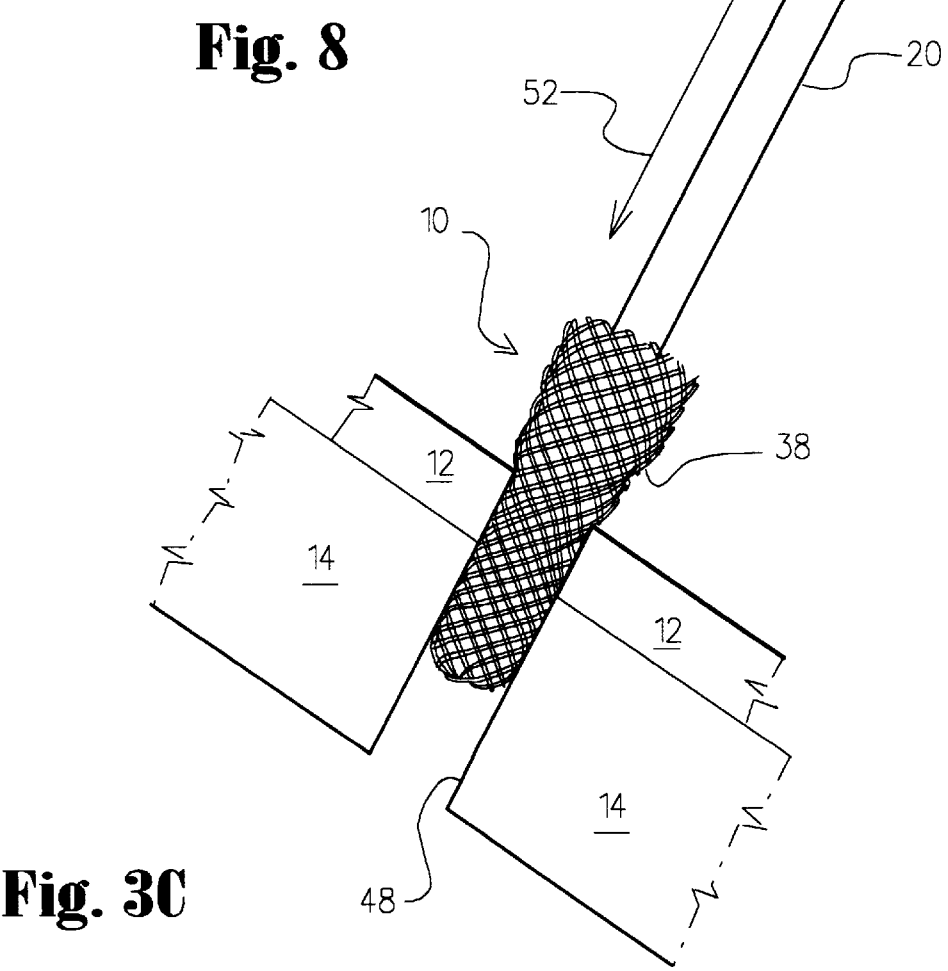
FIG. 3C illustrates the use of the rod to insert a sleeve through a plate and into a hole in the bone.

Turning now to FIGS. 3, 3A, and 3C it will be understood that the helical structure of the fibers 38 that define to sleeve shaped body 26 move relative to one another in response to an axial force in the direction of arrow 40. The movement of the fibers 38 relative to one another will cause a tightening of the spirals in which the fibers 38 are woven, causing a uniform, radial reduction in the diameter or size of the sleeve in the direction of arrows 42. An example of this kind of action can be found in the well-known "Chinese finger trap." Thus, as shown on FIG. 3C, as the sleeve 10 is driven into the hole 48A in the direction of arrow 52, the fibers 38 slide relative to one another and adjust the shape of the sleeve 10 to fill the hole 48A. Once the sleeve 10 has been inserted, the rod 20 may be easily removed, particularly in an embodiment in which the fibers 38 bias the sleeve towards an open arrangement.

It is important to note that while it is contemplated that the fibers 38 may be made of materials having a variety of stiffnesses, the use of fibers 38 which are somewhat resilient allows the modification of the sleeve 10 to achieve different functions with small variations in the structure. For example, with the arrangement shown in FIG. 2, the bias and helical spiral of the fibers 38 tends to open the sleeve body 26, while the arrangement of the fibers 38 at the second end of the body 36 shown on FIG. 3B tends to maintain the sleeve body 26 in a generally closed arrangement.

It should be understood that the woven configuration of the sleeve 10 allows cooperation of the sleeve 10 with the rod 20 during insertion of the sleeve 10 through a hole in an orthopedic device and into a hole in the patient's bone. The woven structure will allow reduction of the diameter or size of the sleeve 10 as it is inserted. Once the sleeve 10 has been inserted to a desired location within the hole, the resiliency of the fibers as well as the fibers' ability to move relative to one another will allow the sleeve 10 to engage the sides of the hole and release any bias against the rod 20, permitting removal of the rod 20.

Figure 4:
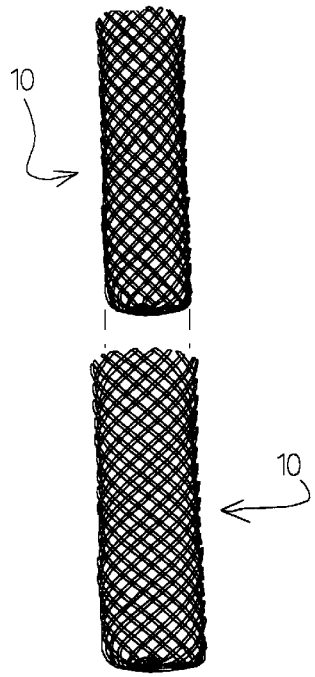
FIG. 4 is a side view of a pair of sleeves being stacked, one inside the other.
Figure 5:
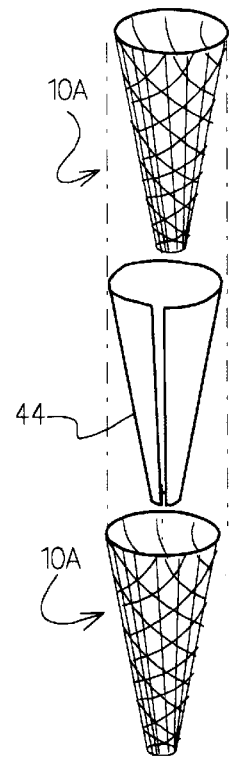
FIG. 5 is a side view of another embodiment of the instant invention, the embodiment including a sleeve with a generally conical shape and two open ends.

Turning now to FIG. 4 and FIG. 5, it will be appreciated that the closing action of the instant invention allows the stacking of several sleeves 10 to provide a thicker stack up for situations where larger amounts of space needs to be taken up. Also shown on FIG. 5 is a sleeve 10A with a generally conical shape, shown together with a layer of a material, referred to herein has an agent material 44, the may be placed between two sleeves 10 that are stacked within one another. This allows the physician to place a layer of an agent material which exhibits bone growth enhancing properties or other biological properties, and thereby providing a customized treatment to the area where the stack of sleeves 10 have been applied.

It is important to note that the resiliency of the fibers 38, and the ability of the woven fibers 38 move relative to one another, produces important new and useful results that could not be achieved with known devices. For example, the resiliency of the fibers 38 can aid in holding and centering the sleeve 10 within the hole in the bone 14. Additionally, the ability of fibers 38 move or slide past one another allows radial of adjustment of the size of the sleeve 10. The radial adjustment of the size sleeve 10 allows uniform build-up of the sleeve material about the fastener 16. Moreover, as discussed above, the resiliency of the fibers 38 will allow the sleeve 10 to open up once inserted in the hole 48, and grip or bias the sleeve 10 against the hole 48, allowing the removal of the rod 20 while leaving the sleeve 10 within the hole 48. Of course, as shown on FIG. 3B it is contemplated that the bias of the fibers 38 may be arranged so that the bias tends to close the sleeve 10, as compared to biasing the fibers 38 to maintain a generally opened sleeve arrangement. In a preferred embodiment of the invention the fibers 38 are made from a suture type material, or of a suture type material that has been impregnated with bone growth stimulating agent, such as a bone morphogenic protein (BMP, or an antibiotic agent to provide protection against infection. The bone morphogenic protein would promote bone growth around the fastener 16. Additionally, it is contemplated that the suture material may be of a bioabsorbable or non-bioabsorbable material or a combination of both.

Figure 6:
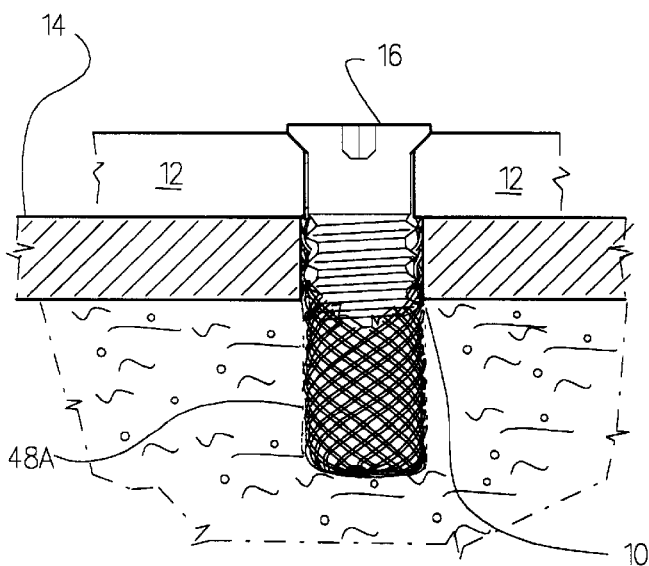
FIG. 6 is a side sectional view with a portion of the sleeve broken away to illustrate the fact that the hole in the bone is larger than the hole in the plate, and the cooperation of the sleeve and that threads of the fastener in taking up the space between the threads of the fastener and the bone.
Figure 7:
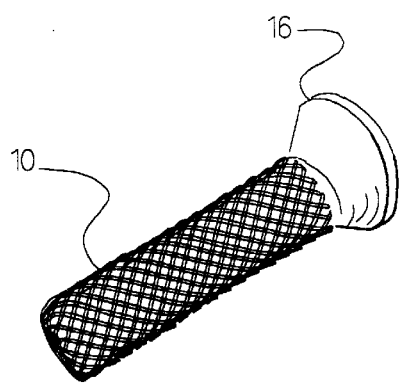
FIG. 7 is a perspective view of a variation of an embodiment of the instant invention, the embodiment shown mounted over a fastener before insertion into the bone.

It will be understood that the instant invention also includes a method for a salvaging a damaged hole. The method includes the steps of providing a woven sleeve 10. The sleeve having an elongated, sleeve shaped body 26. The sleeve shaped body 26 having an interior portion, or surface 30. Then providing an elongated rod 20, and then using the elongated rod 20 for inserting at least one woven sleeve 10 into the into the hole, so that the sleeve remains in the hole. Then, with insertion of the fastener into the sleeve the difference in the size of the damaged hole 48A and the fastener is taken up by the sleeve, as seen in FIG. 6.

It is contemplated that the woven sock, or sleeve 10, can also be used as a container for delivering morselized bone graft material to a desired location. Thus, it will be appreciated that the instant invention presents an important advancement in the art in that traditionally the application of morselized bone graft material is accomplished by placing the graft against the bone with no means for preventing migration or dislodgement of the graft. The previously described woven sleeve 10, or "screw sock," whether manufactured with bone growth enhancing material provides an ideal "bag" or container which can retain the bone graft material at a desired position. Additionally, it is important to note that the surgeon may tailor a mixture of the bone graft material to suit the needs of the patient. Thus, for example, the surgeon may combine bone graft material with bone growth enhancing material within a single sleeve 10, and then suture the sleeve closed to allow placement of the mixture within the sleeve 10 a desired location. Clearly is contemplated that this location may be within yet another sleeve 10, and against a screw, to allow filling of an oblong or irregularly shaped hole.

A sack made from a sleeve 10, as described above, and filled with morselized bone graft material, such as the material known under the trademarks Allograft or the material known under the trademark Autograft, together with BMP (for example) could be introduced through trocars to allow for percutaneous placement of the material at a desired location in the patient's body. Incidentally, the sleeve 10 could also be used prophylactically to provide enhanced purchase for the bone screw when the underlying bone is known to be osteoporotic and brittle. Thus, it will be appreciated that the versatility of the woven sleeve 10 of the instant invention allows the surgeon to carry out many of the tasks that required distinctly different devices, such as the known devices described above. The ability to carry out these functions with a single device made in accordance with the principles taught herein reduces the need to carry a large inventory of these other known devices in the operating room. The elimination of this large variety of devices not only reduces the cost to the hospital, but also reduces the risk of selecting the wrong device where several devices of similar appearance are available.

It will be appreciated that the disclosed invention's ability to accommodate a wide variety screws and other materials and agents to be placed within the body signifies a significant advancement in the art, particularly in the art relating to bone hole reinforcing devices. Additionally, it should be understood that while the invention could be filled with bone graft material, it is contemplated that a variety of materials, whether in particulate form or in consolidated or agglomerated or other form.

Figure 8:
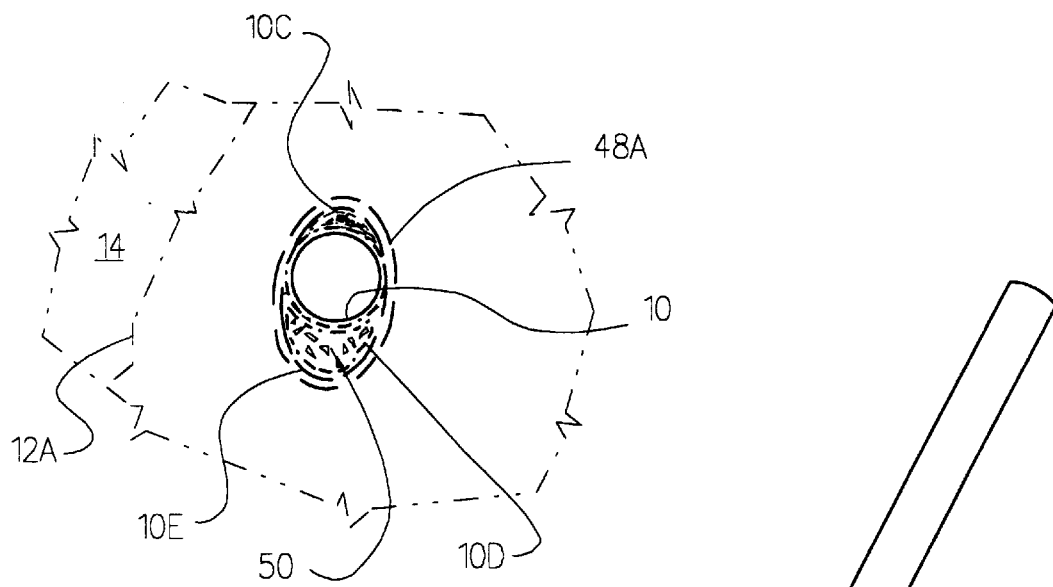
FIG. 8 illustrates the use of several sleeves and other materials to fill a severely damaged hole.

Thus as shown on FIG. 8, a badly damaged hole 48A with a generally oblong shape has been illustrated in the section of bone 14. To salvage this hole it has been necessary for the surgeon to insert a collapsed sleeve 10C on one side of the hole 48A and a filled sleeve 10D, which has been filled with morselized bone graft 50, on another side of the hole 48A. All of these sleeves are held within a retaining sleeve 10E holds the sleeve 10, whose interior outline coincides with the outline of the hole in the orthopedic device 12A being attached. The collapsed sleeve 10C and the filled sleeve 10C lie below the orthopedic device 12A, and thus have been shown in broken lines.

To salvage the hole 48A, the surgeon inserted the retaining sleeve 10E together with the collapsed sleeve 10C and the filled sleeve 10D through the hole in the orthopedic device 12A, and then separated the filled sleeve 10C from the collapsed sleeve 10C with the sleeve 10, after the sleeves have been inserted through the hole in the orthopedic device 12A. The sleeve 10 will thus be backed up or supported by the filled sleeve 10D and the collapsed sleeve 10C. It will be understood that the finished procedure would result in the filled sleeve 10D and the collapsed sleeve 10C being below the plate or orthopedic device 12A, and next to the orthopedic screw which is inserted into the sleeve 10 and used to attach the plate or orthopedic device 12A to the bone.

Thus it can be appreciated that the above described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A device for shimming a hole in a section of bone or shimming a hole in a section of bone for support of an orthopedic screw, the device comprising:

a flaccid elongated sleeve shaped body having an external surface and an internal surface, a first end, a mid portion, and a second end, said mid portion being made from flaccid fibers, the fibers being woven to define the elongated sleeve shaped body, the first end having an opening providing access to the internal surface of the elongated sleeve shaped body, the second end having a section of material extending across the second end of the sleeve in a chord like manner, partially closing the second end of the elongated sleeve, so that the first end elongated of said sleeve shaped body may be inserted into the hole, and so that when the orthopedic screw is inserted into the elongated sleeve, the screw will cooperate with the section of material extending across the elongated sleeve to cause the woven flaccid fibers of the body to move relative to one other to accommodate the orthopedic screw.

2. A device according to claim 1, and further comprising a rod adapted for insertion into the aperture in the first end of said elongated sleeve shaped body and engages the section of material extending across the second end of the sleeve.

3. A device according to claim 1, wherein said woven flaccid fibers are woven in a generally helical manner relative to one another.

4. A device according to claim 3, wherein flaccid said woven fibers comprise a medical fiber material.

5. A device according to claim 4, wherein said medical fiber material is impregnated with a bone growth enhancing material.

6. A system for enhancing the grip of a fastener to be driven into a hole in a bone, the system comprising:

a generally flaccid woven sleeve, the sleeve having an elongated body having an interior portion, the body having a first end and a second end, the first end having an aperture allowing access to the interior portion of the woven sleeve, said woven sleeve being formed from a plurality of flaccid fibers and the second end of the woven sleeve having a section of material extending across the woven sleeve in a chord like manner, partially closing the second end of the sleeve;

so that when said woven sleeve is driven into the hole in the bone, so that the fastener may be inserted into the hole and against the woven sleeve, so that the fibers of the woven sleeve flex to accommodate the fastener and partially fill the hole to enhance the grip between the fastener and the bone.

7. A system according to claim 6, and further comprising an elongated rod, the rod having a first end and a second end, the first end of the rod being smooth and adapted for insertion into the interior portion of the woven sleeve so that upon insertion of said rod into the sleeve shaped body, the rod cooperates with the woven sleeve to support the woven sleeve when inserted into the hole in the bone.

8. A system according to claim 7, wherein said flaccid fibers comprise a suture type material.

9. A system according to claim 8, wherein said suture type material is impregnated with a bone growth enhancing material.

10. A method for enhancing the grip between faster and a material to which fastener is being attached, the method comprising:

creating a hole in the material to which the fastener is to be attached;

providing a generally flaccid woven sleeve, the woven sleeve having an elongated body having an interior portion, the body having a first end and a second end, the first end having an aperture allowing access to the interior of the woven sleeve, said woven sleeve being formed from a plurality of flaccid fibers in a woven relationship, said second end having a section of material extending across the second end of the woven sleeve in a chord like manner, partially closing the second end of the woven sleeve;

providing an elongated rod, the rod having a first end and a second end, the first end of the rod being smooth and adapted for insertion into the woven sleeve against the interior portion of the woven sleeve;

inserting the first end of said elongated rod into the woven sleeve against the interior portion of the woven sleeve to engage the section of material extending across the second end of the woven sleeve;

introducing said woven sleeve into the hole by means of the elongated rod, and then removing the rod from the woven sleeve, so that the woven sleeve remains in the hole;

inserting the fastener into the woven sleeve so that differences in the size of the hole and the fastener are taken up by the woven sleeve.

11. A method according to claim 10, wherein said woven flaccid fibers are woven in a generally helical arrangement relative to one another.

12. A method according to claim 11, and further comprising the step of providing a second woven sleeve, and inserting the second woven sleeve into the first woven sleeve.

13. A method according to claim 11, and further comprising the step of providing a sleeve of agent material, and inserting the sleeve of agent material into the woven sleeve.

14. A method according to claim 13, and further comprising the step of providing a second woven sleeve, and inserting the second woven sleeve into the sleeve of agent material.

15. A method according to claim 12, wherein said woven flaccid fibers comprise a suture type material.

16. A method according to claim 15, wherein said suture material is impregnated with a bone morphogenic protein.

* * * * *